United States Patent
Adamson

(10) Patent No.: US 7,712,152 B2
(45) Date of Patent: May 11, 2010

(54) BREAST EXPOSED UNDER GARMENT

(76) Inventor: Jodie L. Adamson, 12554 Sidney Freyburg Rd., Anna, OH (US) 45302

( * ) Notice: Subject to any disclaimer, the term of this patent is extended or adjusted under 35 U.S.C. 154(b) by 0 days.

(21) Appl. No.: 11/824,940

(22) Filed: Jul. 2, 2007

(65) Prior Publication Data
US 2008/0172771 A1 Jul. 24, 2008

(51) Int. Cl.
*A41D 1/20* (2006.01)
(52) U.S. Cl. .......................................... 2/104
(58) Field of Classification Search ............. 2/113, 2/114, 115, 104, 73; 450/1, 36
See application file for complete search history.

(56) References Cited

U.S. PATENT DOCUMENTS

| | | | | |
|---|---|---|---|---|
| 206,906 | A * | 8/1878 | Strauss | 450/36 |
| 1,136,727 | A * | 4/1915 | Smith | 450/36 |
| 2,406,699 | A * | 8/1946 | Lustig | 450/64 |
| 3,203,424 | A * | 8/1965 | Garutso | 450/68 |
| 3,527,231 | A * | 9/1970 | Catanese et al. | 450/60 |
| 3,773,052 | A * | 11/1973 | Belardinelli | 450/41 |
| 3,967,335 | A * | 7/1976 | Rhoads | 5/632 |
| 4,004,294 | A * | 1/1977 | Pinch | 2/104 |
| 4,222,387 | A * | 9/1980 | Tetu | 450/36 |
| 4,446,572 | A * | 5/1984 | Lindquist | 2/104 |
| 4,566,136 | A * | 1/1986 | Echols | 2/104 |
| 4,663,782 | A * | 5/1987 | Knox et al. | 2/104 |
| 5,103,501 | A * | 4/1992 | Meisels | 2/113 |
| 5,182,813 | A * | 2/1993 | Booze | 2/104 |
| 5,461,725 | A * | 10/1995 | Witczak | 2/104 |
| 5,611,086 | A * | 3/1997 | Eggen | 2/104 |
| 5,772,492 | A * | 6/1998 | Erwin | 450/30 |
| 6,000,993 | A * | 12/1999 | Erwin | 450/7 |
| 6,083,079 | A * | 7/2000 | Pearson | 450/1 |
| 6,264,529 | B1 * | 7/2001 | Logue | 450/36 |
| 6,282,719 | B1 * | 9/2001 | Vera et al. | 2/78.1 |
| 6,319,092 | B1 * | 11/2001 | Leyhe et al. | 450/36 |
| 6,361,398 | B1 * | 3/2002 | Knapp | 450/37 |
| 6,581,209 | B2 * | 6/2003 | Bramhan | 2/48 |
| 6,659,841 | B2 * | 12/2003 | Raimondo | 450/36 |

(Continued)

OTHER PUBLICATIONS

Nursing Chic, One Hot Mamma, http://onehotmama.com.chic.htm Feb. 6, 2002.*

(Continued)

*Primary Examiner*—Alissa L Hoey
(74) *Attorney, Agent, or Firm*—MacMillan, Sobanski & Todd, LLC

(57) ABSTRACT

A garment includes a body portion having a neck opening and a pair of arm openings formed therethrough. First and second breast exposing openings are formed through the body portion that are adapted to encircle and completely expose the breasts of the wearer. Thus, the body portion is free from any type of obstructive covering over the first and second breast exposing openings. The body portion may be formed from a single tube-shaped piece of material or it may be formed from a plurality of pieces of material. If desired, a bodice portion may extend from body portion. The body portion and the bodice portion may be formed from a single tube-shaped piece of material or from a plurality of pieces of material. The first and second breast exposing openings may have respective aesthetic decorations, such as decorative flower petals, provided thereabout.

14 Claims, 1 Drawing Sheet

U.S. PATENT DOCUMENTS

| | | | |
|---|---|---|---|
| 6,983,489 B2* | 1/2006 | Caprio | 2/69 |
| 39,539 A1* | 1/2008 | Lucock | 2/104 |
| 2005/0026540 A1* | 2/2005 | Schneider et al. | 450/36 |
| 2005/0028243 A1* | 2/2005 | Polzin | 2/104 |
| 2005/0085160 A1* | 4/2005 | Johnstone | 450/36 |
| 2005/0208873 A1* | 9/2005 | Rothman | 450/36 |
| 2007/0105481 A1* | 5/2007 | Scholz | 450/3 |
| 2007/0124845 A1* | 6/2007 | McCoy | 2/104 |

OTHER PUBLICATIONS www.buciolingerie.com Teddy, X2497; Jul. 1, 2001.*

* cited by examiner

BREAST EXPOSED UNDER GARMENT

CROSS-REFERENCE TO RELATED APPLICATIONS

This application claims the benefit of U.S. Provisional Application No. 60/465,707, filed Apr. 26, 2003, the disclosure of which is incorporated herein by reference.

BACKGROUND OF THE INVENTION

This invention relates in general to under garments. In particular, this invention relates to an improved structure for an under garment that can, for example, be worn by a woman having a need to have her breast area completely exposed for easy access thereto, such as to facilitate breast feeding.

There is a need among breast feeding women for an under garment that will expose the breast to facilitate nursing a baby without having to disrobe or partially disrobe. A variety of outer garments are available that are specifically designed for breast feeding women. However, these outer garments tend to be either costly, limited in style and selection, or both. Furthermore, many women find it inconvenient to purchase a whole new wardrobe of shirts, blouses, dresses, and upper garments that are designed specifically for breast feeding.

Prior art approaches to breast feeding garments are typically characterized by either (1) a garment featuring slits or vents for selective exposure of the breast or (2) a garment featuring patches, flaps, or connecting elements (such as buttons) that interconnect the garment in such a way that the breast is normally covered, and a flap can be lifted or shifted that would allow the breast or bra to be exposed. However, garments having slits usually require either cumbersome adjustment of clothing, the breast, or both. Also, a slit does not lend itself to any type of form fitting design, but rather is usually incorporated into an A-line type loose garment. Patches and flaps are also cumbersome, obvious, and often require manipulation of the connecting elements for exposure of the breast.

One earlier proposal for a nursing garment is disclosed in U.S. Pat. No. 3,449,763 to Grate, which issued on Jun. 17, 1969. This patent discloses a garment that simulates a slip under garment. The openings to expose the breast are closed or opened by means of a slide fastener construction. Although this garment can be worn as an under garment, it is disadvantageous to a woman in need of quick access to her breast because the slide fastener construction creates the need for further manipulation of her breast feeding apparel, making the process difficult for her and causing delay in feeding the hungry baby. Another proposal is disclosed in U.S. Pat. No. 5,461,725 to Witczak, which issued on Oct. 31, 1995. In this patent, the openings to expose the breast are closed or opened by means of a male/female snap construction. Like the Grate patent, this garment also has the disadvantage of requiring a more extensive process of preparing the breast to feed the sometimes impatient baby. Proposals disclosed in U.S. Pat. No. 5,182,813 to Booze, which issued on Feb. 2, 1993, and U.S. Pat. No. 4,208,743 to Whitcraft, which issued on Jun. 24, 1980, both consist of openings to expose the breast, yet include cover panels that make them cumbersome and bulky to be worn as an under garment. U.S. Pat. No. 6,361,398 to Knapp, which issued on Mar. 26, 2002, discloses a brassiere garment consisting of nursing holes, but not offering coverage for the upper torso area below the breasts. Another prior art approach is disclosed in U.S. Pat. No. 5,611,086 to Eggen, which issued on Mar. 18, 1997. The Eggen patent discloses an under garment with a pair of openings therein through which the nursing mother's breast will protrude. However, the disadvantage to this garment is that it is attached to a vest that includes a pair of flaps designed to be a sleeping gown for a nursing woman. Not only does this garment require the manipulation of flaps to retrieve the breast, but this garment also could not be used as an under garment. Another disadvantage of the prior art affects the woman who is returning to work and does not desire to wear nursing clothes during the day. For the breast feeding woman who pumps her breasts during the day, a nursing garment is not practical. She will usually wear certain office attire or wardrobe suitable to her profession. Yet, there is a need to have coverage and protection during the times of breast pumping. The prior art does not offer her a solution. What is needed, therefore, is an under garment that will offer a woman coverage when she is pumping, yet leaves her breasts uncovered for easy access to make the pumping process more comfortable and easy. None of the above-mentioned prior art garments leave the breast completely exposed with no flaps, fasteners, or slits to contend with and, at the same time, is close fitting, lightweight, constructed with a low neck line, and can be worn under virtually any other garment to offer coverage of the desired body parts, yet provide easy access to the breast. What is also needed is a garment that is free from any type of obstructive covering over the breast or bra to make access to the breast quick and easy by allowing the breast or bra to remain completely exposed. Ideally, this garment would provide coverage for the section of the torso she does not desire to be exposed and also offer the woman protection from drafts or exposure.

SUMMARY OF THE INVENTION

The breast exposed under garment of this invention simulates an under garment comprising a close fitting bodice for the upper torso with a pair of openings encircling and completely exposing the breasts of the wearer. The invention optionally provides decorative flower petals or other decorations surrounding each breast opening for aesthetic features. Further objects and advantages of this invention will become apparent from a consideration of the drawings and ensuing description.

This invention provides a novel solution to the problems discussed with the above-mentioned prior art. It is, therefore, an object of this invention to provide an under garment that can be worn under any clothing article, either on top of a bra or without a bra, and that will leave the breast area completely exposed by means of openings for convenient and quick access to the breast. This object also includes providing a nursing under garment free from flaps, fasteners, or slits and the like, thereby making it easy to access her breast for quick facilitation of nursing. In the prior art, the woman would have to first open the flap or slit, then manipulate the opening to bring the breast through before latching the baby on to nurse. For the nursing woman, a whole step is eliminated. The breast is already exposed and in place, and she need only latch the baby on. This advantage over the prior art offers the mother an easier and more pleasurable breast feeding experience and offers the hungry infant quicker dinners. Another object of the present invention is to provide an under garment with either simple holes that will encompass the breast or holes with the fresh approach of decorative flower petals or other aesthetic decorations encircling which will make the garment pleasurable to wear.

During the breast feeding experience the woman's breasts become a focus of her life. Every couple of hours, they become the main food source for her growing infant. Her breasts are exposed more than any other time in her life, especially to those living with her. The decorative openings of the invention privately create the feeling of celebrating her breasts and her breast feeding experience. This novel and fun feature is not accomplished in the prior art.

A further object of the present invention is to provide a garment in which the breast can be completely exposed for any purpose other than breast feeding, such as breast pumping or to change the dressing after breast surgery. For the woman who needs to pump her breasts after returning to work, this invention offers a definite advantage. A woman who returns to work will usually not wear nursing apparel. She will wear attire suitable to her profession. The garment of this invention offers her the comfort and coverage she needs while pumping, yet does not affect her professional wardrobe. Still another object of the present invention is to provide a garment that will offer warmth and coverage to the torso area below and surrounding the breasts as she opens or lifts her upper outer garment to breast feed or expose her breast for any other reason. This object provides a modest covering for the areas of her body she does not desire to be exposed. This object additionally offers protection to a nursing woman from the chill or pinching to her mid-torso from the hands of the infant when held in the nursing position.

A woman who has recently given birth usually is somewhat self-conscience about her middle section. After all, this is the area of her body that was stretched to at least twice its size to accommodate a fetus. It will take her some time to get her waist back in shape. The breast exposed under garment of the present invention offers her peace of mind that as she lifts up her shirt to breast feed, her waist is completely covered, offering her freedom from discomfort and embarrassment. This will make her breast feeding experience much more relaxed and enjoyable.

Yet a further object of the present invention is to provide a garment which is close fitting, yet lightweight and comfortable to be worn under any article of clothing. Another object of the present invention is to provide a garment that is constructed with a low neck line to make it unnoticeable when worn under any blouse, shirt, dress, or other upper outer garment. Yet another object of this invention is to provide a garment with a bodice that is long enough to be worn tucked into her bottom outer garment if she desires. A further object of the invention is to provide an under garment that may be made sleeveless or with the option of having sleeves of any length for extra warmth and coverage. Still another object of the this invention is to provide a garment that is inexpensive to manufacture. As compared to the prior art, this invention has a much simpler design and will not be as costly to purchase as the prior art. Cost efficiency is also achieved by this garment because it eliminates her need to purchase separate specially designed breast feeding clothing. Not only will this give her the benefit of wearing her usual clothing, it will give her a greater wardrobe selection because she will not be limited to breast-feeding clothing only.

Yet a further object of the invention is to provide a nursing garment that is simple in design, rugged in construction, easy to use, and efficient in operation. An innovative garment in accordance with this invention provides solutions to deficiencies and other disadvantages mentioned of the prior art.

Various other objects and advantages of this invention will become apparent to those skilled in the art from the following detailed description of the preferred embodiments, when read in light of the accompanying drawings.

DETAILED DESCRIPTION OF THE PREFERRED EMBODIMENTS

Figure 1:
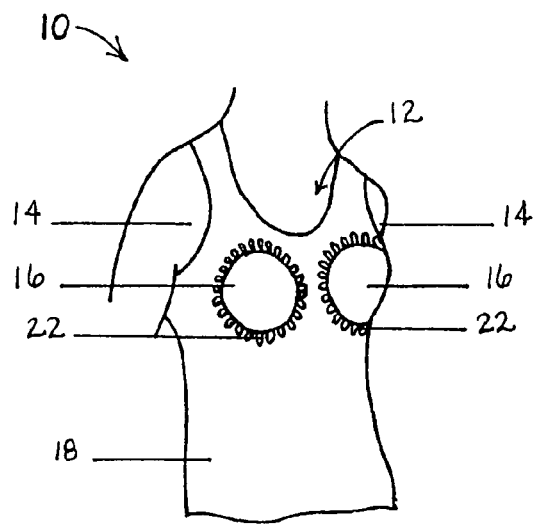
FIG. 1 is a front perspective view of a first embodiment of a breast exposed under garment in accordance with this invention.

Referring now to the drawings, there is illustrated in FIG. 1 a first embodiment of a breast exposed under garment, indicated generally at 10, in accordance with a first embodiment of this invention. The illustrated garment 10 includes a body portion 11 having a head opening, indicated generally at 12, and left and right arm holes 14 formed therethrough. The head opening 12 may, if desired, be constructed having a relatively low neckline, as shown in FIG. 1. This feature offers the advantage of wearing the garment 10 under an outer garment having any type of neckline. For a woman who is wearing the under garment 10, it is important that the under garment 10 stay in position under her clothing and not hang out where it can be seen. The low neck line will eliminate this problem. Although the garment 10 can be constructed having a low neck line, it could also have a neck line of any length, just as it may also be constructed with sleeves of any length, as opposed to being sleeveless as shown in FIG. 1.

The garment 10 also has left and right breast openings 16 formed therethrough that expose the breasts of the woman wearing the garment 10 and offer the woman quick and easy access to her breasts for the purpose of nursing, pumping, changing a dressing after surgery, or any other reason that is facilitated by her breast being exposed. The breast exposing openings 16 eliminate the need for the woman to reach under her outer garment and manipulate any flaps, slits, or fasteners to gain access to her breasts.

For the breast feeding woman, this is of extreme importance. A hungry infant is often impatient while waiting to latch on to the breast. With this innovative feature of having the breasts completely exposed by the left and right breast openings 16, the woman will simply reach up, unlatch her bra if necessary, and place the baby to the breast. A whole step is eliminated. In the prior art, the woman would need to first open the flap or slit, then manipulate the slit to bring the breast through the opening in order to nurse the infant. With the breast exposed openings 16 of this invention, both breasts are already exposed and in position though the respective openings 16, so one whole cumbersome process is eliminated. The breast exposed openings 16 also offer a great convenience for the woman who needs to pump her breasts. A woman who returns to work and needs to pump her breasts does not usually wear nursing garments. Instead, she will wear a non-nursing outfit suitable to her profession. The breast exposed under garment 10 of this invention is the perfect solution for her because it will give her the coverage she desires, yet still affords her the convenience of access to her breasts for quick and easy pumping.

The breast exposed under garment 10 can, if desired, include a bodice including a front portion 18 and a rear portion 20 (see FIGS. 3 and 4) that extends downwardly from the body portion 11. The bodice may be formed from either the same or different material as the remainder of the garment 10. The garment 10 and the bodice can be formed from any desired material or combination of materials such as, for example, from a flexible, stretchable fabric, such as cotton ribbing or tricot materials. The bodice may be formed from any material that can be stretched to gain access to the bra if necessary, yet provide a close, comfortable fit to the wearer. This close fit creates the ability to be worn under any outer garment without causing bulk. The bodice is also preferably formed having a length that will either remain at the waist or extend down around the hips to enable the wearer to comfortably tuck in the garment 10 to her lower outer garment.

Figure 2:
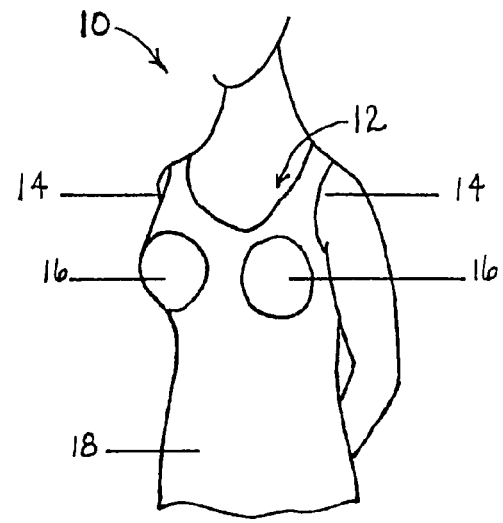
FIG. 2 is a front perspective view of a second embodiment of a breast exposed under garment in accordance with this invention.

In the embodiment of the invention illustrated in FIG. 2, neither of the left and right breast openings 16 are decorated, but rather have respective simple seams, hems, or trims that encircle each of the openings 16. The seams function to reinforce the edges of the openings 16, offer structural integrity to the openings 16, and prevent fraying of the material used to form the upper body portion of the breast feeding under garment, particularly if such material is stretched during the breast feeding process. This feature will satisfy a woman who would like a relatively simple design or a woman who will need to wear the garment under a lightly colored blouse.

Figure 3:
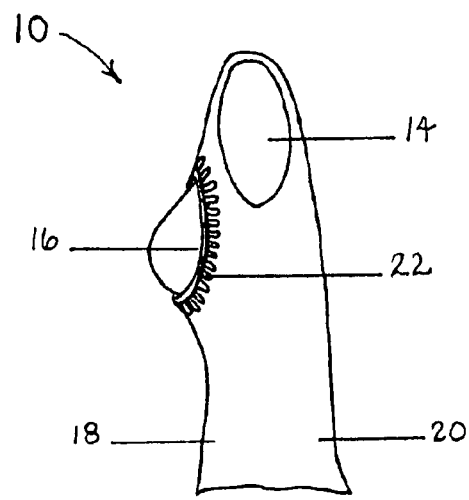
FIG. 3 is a side elevational view of the second embodiment of the breast exposed under garment illustrated in FIG. 2.

FIGS. 2 and 3 illustrate a second embodiment of a breast exposed under garment, indicated generally at 10', in accordance with this invention. The second embodiment of the garment 10' is, in large measure, similar to the first embodiment illustrated in FIG. 1, and like reference numbers are used to indicate similar structures. The second embodiment of the garment 10' is provided with aesthetic decorations 22 that encircle either or both of the left and right breast openings 16. In the illustrated embodiment, the aesthetic decorations 22 are shown as decorative flower petals. However, the aesthetic decorations 22 may have any desired shape or form. The aesthetic decorations 22 may completely encircle each of the left and right breast openings 16 as shown or, alternatively, may only partially encircle each of such openings 16.

In the prior art, the openings for the breast are either simple with no decorations, or the breast openings are incorporated into the garment to be hidden. The breast exposed under garment 10 of this invention has a fresh approach to the breast openings 16 by decorating them with pleasing features. Breast feeding is a very special time in a woman's life. Her breasts definitely become a main focus in her life. This innovative feature privately draws attention to her breasts and creates the feeling of celebrating her breast feeding experience. This novel feature of the invention makes the garment 10 fun to wear and is not available in the prior art.

Figure 4:
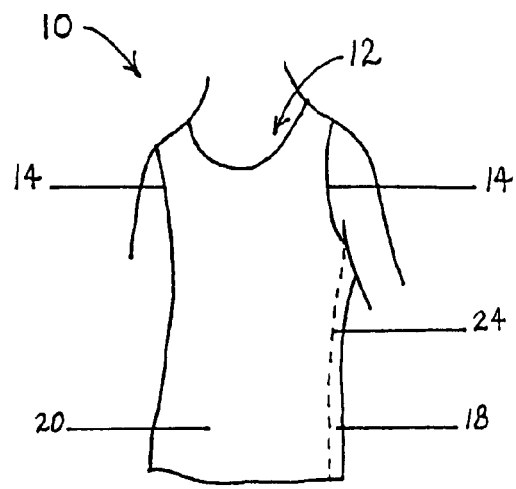
FIG. 4 is a rear perspective view of a third embodiment of a breast exposed under garment in accordance with this invention.

FIG. 4 illustrates a third embodiment of a breast exposed under garment, indicated generally at 10", in accordance with this invention. The third embodiment of the garment 10" is, in large measure, similar to the first embodiment illustrated in FIG. 1, and like reference numbers are used to indicate similar structures. In the third embodiment, the body portion 11 and the front and rear portions 18 and 20 of the bodice of the under garment 10" are formed from separate panels of material. As a result, a pair of seams 24 (only one is illustrated) are provided in the body portion 11 and the bodice of the garment 10". This is different from the first and second embodiments of this invention illustrated in FIGS. 1, 2, and 3, wherein the body portion 11 and the front and rear portions 18 and 20 of the bodice of the under garment 10 are formed from a single panel of material, such as by using a fabric that is generally tube-shaped. The garment 10" may be formed from any desired panels of material that are secured together in any desired manner.

The simple construction of each of the garments shown in FIGS. 1 through 4 holds a major advantage over prior art. It is inexpensive to manufacture as compared to the more complex designs of the prior art. Thus, the foregoing is considered as illustrative only of the principles of the invention. Further, since numerous modifications and changes will readily occur to those skilled in the art, it is not desired to limit the invention to the exact construction and operation shown and described. Accordingly, all suitable modifications and equivalents of this invention are considered to fall within the scope of the invention. For example, the breast openings 16 may have any one of a variety shapes, such as circular, oval, tear-drop, rectangular, triangular, and the like. The sleeves can consist of any length, including sleeveless as shown in FIGS. 1 through 4. Also, the garment can be made in any size or color. Thus, the scope of the invention should be determined by the appended claims and their legal equivalents, rather than by the examples given.

What is claimed is:

1. A breast feeding under garment comprising:

a generally tube-shaped upper body portion that is adapted to cover an upper torso of a wearer and a tube-shaped lower bodice portion having a lower end defining a single opening that is adapted to extend about the waist or the hips of the wearer to enable the wearer to tuck the under garment in a lower garment that is worn by the wearer;

a neck opening formed through said generally tube-shaped upper body portion of said breast feeding under garment;

a pair of arm openings formed through said generally tube-shaped upper body portion of said breast feeding under garment; and first and second breast exposing openings formed through said generally tube-shaped upper body portion of said breast feeding under garment and having circumferential edges, said first and second breast exposing openings being adapted to completely expose the breasts of the wearer to facilitate a breast feeding process by the wearer, said generally tube-shaped upper body portion being free from any type of obstructive covering over said first and second breast exposing openings formed therethrough, said first and second breast exposing openings having respective seams encircling the openings that reinforce said edges of said openings, offer structural integrity to said openings, and prevent fraying of material used to form said upper body portion of said breast feeding under garment, particularly if said material is stretched during the breast feeding process; wherein said body portion includes no structures that cover or partially cover said first and second breast exposing openings.

2. The garment defined in claim 1 wherein said body portion is formed from a single piece of material.

3. The garment defined in claim 2 wherein said body portion is formed from a tube-shaped piece of material.

4. The garment defined in claim 1 wherein said body portion is formed from a plurality of pieces of material.

5. The garment defined in claim 1 further including a bodice portion that extends from said body portion.

6. The garment defined in claim 5 wherein said body portion and said bodice portion are formed from a single piece of material.

7. The garment defined in claim 6 wherein said body portion and said bodice portion are formed a tube-shaped piece of material.

8. The garment defined in claim 5 wherein said body portion and said bodice portion are formed from a plurality of pieces of material.

9. The garment defined in claim 1 wherein said first and second breast exposing openings have respective aesthetic decorations provided thereabout.

10. The garment defined in claim 9 wherein said aesthetic decorations are decorative flower petals.

11. The garment defined in claim 1 wherein each of said first and second breast openings are circular in shape.

12. The garment defined in claim 1 wherein said body portion is sleeveless.

13. The garment defined in claim 1 wherein said neck opening defines a low neck line.

14. A breast feeding under garment comprising:

a generally tube-shaped upper body portion that is adapted to cover an upper torso of a wearer and a tube-shaped lower bodice portion having a lower end defining a single opening that is adapted to extend about the waist or the hips of the wearer to enable the wearer to tuck the under garment in a lower garment that is worn by the wearer;

a neck opening formed through said generally tube-shaped upper body portion of said breast feeding under garment;

a pair of arm openings formed through said generally tube-shaped upper body portion of said breast feeding under garment; and first and second breast exposing openings formed through said generally tube-shaped upper body portion of said breast feeding under garment and having circumferential edges, said first and second breast exposing openings being adapted to completely expose the breasts of the wearer to facilitate a breast feeding process by the wearer, said generally tube-shaped upper body portion being free from any type of obstructive covering over said first and second breast exposing openings formed therethrough, said first and second breast exposing openings having respective seams encircling the openings that reinforce said edges of said openings, offer structural integrity to said openings, and prevent fraying of material used to form said upper body portion of said breast feeding under garment, particularly if said material is stretched during the breast feeding process; wherein said body portion includes no structures that cover or partially cover said first and second breast exposing openings; and wherein said lower bodice portion extends from said upper body portion by a length that will either remain at a waist or extend down around hips of a wearer to enable the wearer to comfortably tuck into a bottom outer garment.

* * * * *